(12) United States Patent
Nishi

(10) Patent No.: US 12,430,753 B2
(45) Date of Patent: Sep. 30, 2025

(54) PATHOLOGICAL DIAGNOSIS SUPPORT SYSTEM AND PATHOLOGICAL DIAGNOSIS SUPPORT DEVICE

(71) Applicant: PHC Holdings Corporation, Tokyo (JP)

(72) Inventor: Megu Nishi, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 17/767,700

(22) PCT Filed: Nov. 20, 2020

(86) PCT No.: PCT/JP2020/043364
§ 371 (c)(1),
(2) Date: Apr. 8, 2022

(87) PCT Pub. No.: WO2021/117466
PCT Pub. Date: Jun. 17, 2021

(65) Prior Publication Data
US 2024/0119585 A1   Apr. 11, 2024

(30) Foreign Application Priority Data
Dec. 10, 2019   (JP) .................. 2019-222977

(51) Int. Cl.
*G06T 7/00*   (2017.01)
*G16H 50/20*   (2018.01)

(52) U.S. Cl.
CPC ........... *G06T 7/0012* (2013.01); *G16H 50/20* (2018.01); *G06T 2207/30096* (2013.01)

(58) Field of Classification Search
CPC ......... G06T 7/0012; G06T 2207/30096; G06T 1/00; G16H 50/20; G16H 40/67;
(Continued)

(56) References Cited

U.S. PATENT DOCUMENTS

| 5,807,256 A | 9/1998 | Taguchi et al. |
| 2005/0143641 A1* | 6/2005 | Tashiro ................. G06T 19/00 600/407 |

(Continued)

FOREIGN PATENT DOCUMENTS

| JP | 6-251038 | 9/1994 |
| JP | 2012-245090 | 12/2012 |

(Continued)

OTHER PUBLICATIONS

Machine translation for WO 2012/102069 (Year: 2012).*

(Continued)

*Primary Examiner* — Qian Yang
(74) *Attorney, Agent, or Firm* — Wenderoth, Lind & Ponack, L.L.P.

(57) ABSTRACT

This pathological diagnosis support system comprises an image diagnosis server and a pathologist's personal computer. The image diagnosis server uses an image analysis unit to set confirmation frames in which the abnormality score exceeds a threshold value, assigns a frame number of "1," "2," or "3" to each of the confirmation frames, and sends setting information about the pathological diagnosis image and the confirmation frames and the frame number "1," "2," or "3" of the confirmation frames to the pathologist's personal computer. When the pathological diagnosis image is displayed on a display unit, the personal computer controls the display unit so that the confirmation frames and the frame number "1," "2," or "3" are displayed within the pathological diagnosis image, and the frame number "1," "2," or "3" is displayed on the outside of the pathological diagnosis image.

2 Claims, 17 Drawing Sheets

(58) Field of Classification Search
CPC ........ G16H 30/20; G16H 30/40; G16H 50/70; G01N 33/48; G01N 33/483
See application file for complete search history.

(56) References Cited

U.S. PATENT DOCUMENTS

| | | |
|---|---|---|
| 2012/0300997 A1 | 11/2012 | Li |
| 2013/0315456 A1 | 11/2013 | Marugame |
| 2014/0122515 A1* | 5/2014 | Lee .......................... G16Z 99/00 707/758 |
| 2019/0156476 A1 | 5/2019 | Yoshida et al. |

FOREIGN PATENT DOCUMENTS

| | | | |
|---|---|---|---|
| JP | 2018-454 | | 1/2018 |
| JP | 2019-95212 | | 6/2019 |
| WO | 2012/105281 | | 8/2012 |
| WO | WO 2012/102069 | * | 8/2012 |
| WO | WO 2012/157201 | * | 7/2014 |

OTHER PUBLICATIONS

Machine translation for WO 2012/157201 (Year: 2012).*
International Search Report issued Feb. 9, 2021 in International (PCT) Application No. PCT/JP2020/043364.
International Preliminary Report on Patentability issued Apr. 28, 2021 in International (PCT) Application No. PCT/JP2020/043364.

* cited by examiner

PATHOLOGICAL DIAGNOSIS SUPPORT SYSTEM AND PATHOLOGICAL DIAGNOSIS SUPPORT DEVICE

TECHNICAL FIELD

The present invention relates to a pathological diagnosis support system and a pathological diagnosis support device used for pathological diagnosis of cancer, for example.

BACKGROUND ART

Pathological diagnosis of cancer is performed by a pathologist who visually checks a pathological diagnosis image obtained by scanning a pathological diagnosis specimen (a specimen prepared for the purpose of pathological diagnosis from a specimen collected from a patient). At this time, the pathologist blows up and observes any suspicious area of the pathological diagnosis image to confirm the pathology.

In other words, if the image display is not enlarged, the pathologist may overlook the presence of small cancer cells, and the pathologist has to spend a very long time to make this pathological diagnosis.

In view of this, in order to reduce the burden on the pathologist, a method has been proposed in which the pathological diagnosis image is divided into a plurality of divided images, and anything that may be an abnormality in each divided image is highlighted in a different color (as a prior document similar to this, see Patent Literature 1 below, for example).

CITATION LIST

Patent Literature

Patent Literature 1: JP-A 2019-95212

SUMMARY

Technical Problem

With the above-mentioned prior art, the pathological diagnosis image displayed on the display unit is highlighted in a different color. Therefore, by focusing on this colored portion, the pathologist will be less worried about overlooking an abnormal portion, and thus the burden on the pathologist can be reduced.

Nevertheless, if the point of interest is extremely small in the pathological diagnosis image, it may be overlooked even if the point of interest is colored.

That is, since a pathological diagnosis image consists of a mixture of various colors and tissue morphologies, it is difficult for a pathologist to reliably notice such a small point. Accordingly, the pathologist in the past had to check a pathological diagnosis image by concentrating on the entire image, so it was impossible to sufficiently reduce the burden on the pathologist.

In view of this, it is an object of the present invention to provide a pathological diagnosis support system and a pathological diagnosis support device with which the burden on a pathologist can be reduced.

Solution to Problem

In order to achieve this object, an image diagnosis server that analyzes an pathological diagnosis image, and a pathologist terminal that communicates with the image diagnosis server are provided. The image diagnosis server has an image analysis unit that analyzes a pathological diagnosis image, and a first control unit to which the image analysis unit is connected. The first control unit uses the image analysis unit to divide the pathological diagnosis image into a plurality of divided images and calculate an abnormality score for each divided image, sets a confirmation frame including a divided image whose abnormality score exceeds a threshold value and assigns a frame number to each confirmation frame, and sends to the pathologist terminal setting information about the confirmation frame and the pathological diagnosis image, and the frame number of the confirmation frame. The pathologist terminal has a display unit and a second control unit. The second control unit controls the display unit so that when the pathological diagnosis image is displayed on the display unit, the confirmation frame and the frame number of the confirmation frame are displayed in the pathological diagnosis image, and the frame number of the confirmation frame is displayed outside the pathological diagnosis image.

Effects

With the configuration of the present invention, when a pathological diagnosis image is displayed on the pathologist terminal of a pathologist, a confirmation frame and a frame number are displayed in the pathological diagnosis image, and a frame number corresponding to the frame number displayed in the pathological diagnosis image is displayed outside the pathological diagnosis image.

Accordingly, the pathologist can immediately recognize that there is a point of interest to be checked in the pathological diagnosis image by looking at the frame number displayed on the outside of the pathological diagnosis image. Then, the pathologist can immediately ascertain the position and size of the confirmation frame in the pathological diagnosis image from the frame number and the confirmation frame displayed in the pathological diagnosis image.

Consequently, the pathologist can concentration on the confirmation frame corresponding to the frame number displayed on the outside of the pathological diagnosis image, so the burden on the pathologist can be reduced.

That is, since a frame number and a confirmation frame are assigned to the attention point that is to be checked, the pathologist is under less strain, having more confidence and assurance that his or her confirmation will not overlook the attention points.

DESCRIPTION OF EMBODIMENTS

An embodiment of the present invention will now be described with reference to the appended drawings.

Embodiment 1

Figure 1:
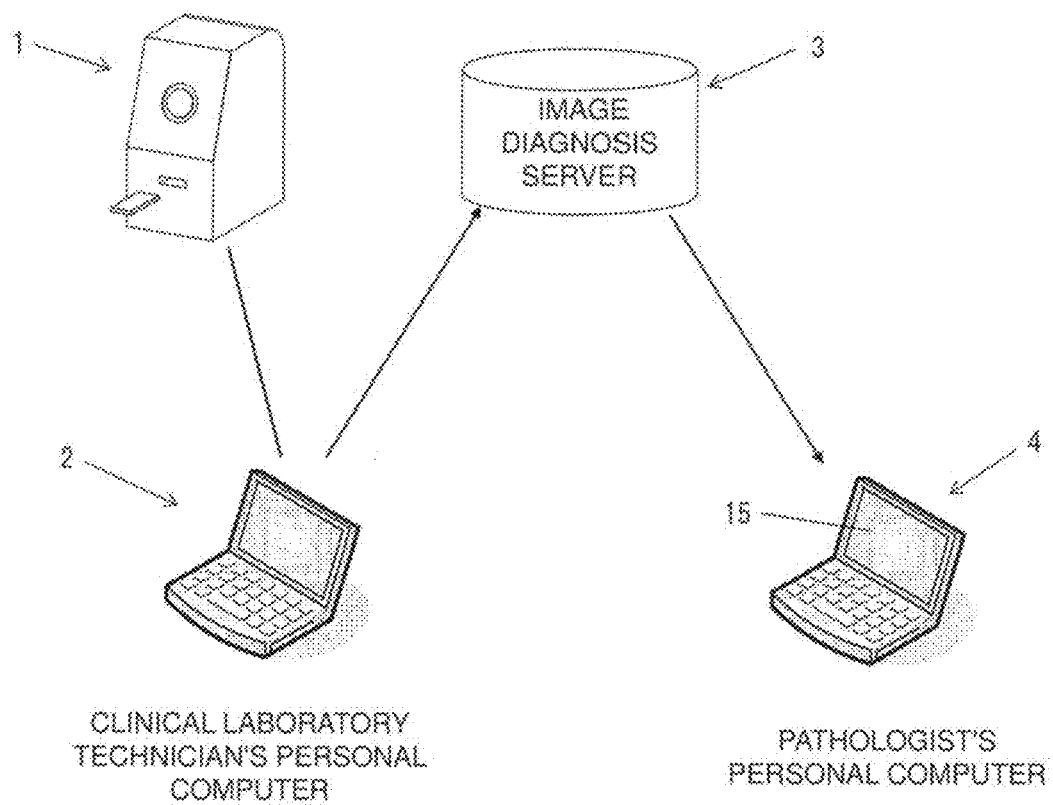
FIG. 1 is a diagram showing the configuration of a pathological diagnosis support system according to Embodiment 1 of the present invention.

FIG. 1 shows the configuration of the pathological diagnosis support system of this embodiment.

An image scanner 1 is connected to a personal computer 2 belonging to a clinical laboratory technician, scans a pathological diagnosis sample (a sample collected from a patient for the purpose of pathological diagnosis), and sends the resulting pathological diagnosis image to the clinical inspection technician's personal computer 2.

The personal computer 2 transmits the pathological diagnosis image obtained by the image scanner 1 to an image diagnosis server 3.

The image diagnosis server 3 sends the pathological diagnosis image and the analysis result obtained by analyzing the pathological diagnosis image to the pathologist's personal computer 4 (an example of a pathologist terminal).

The pathologist makes a pathological diagnosis using the pathological diagnosis image sent to the personal computer 4.

Figure 2:
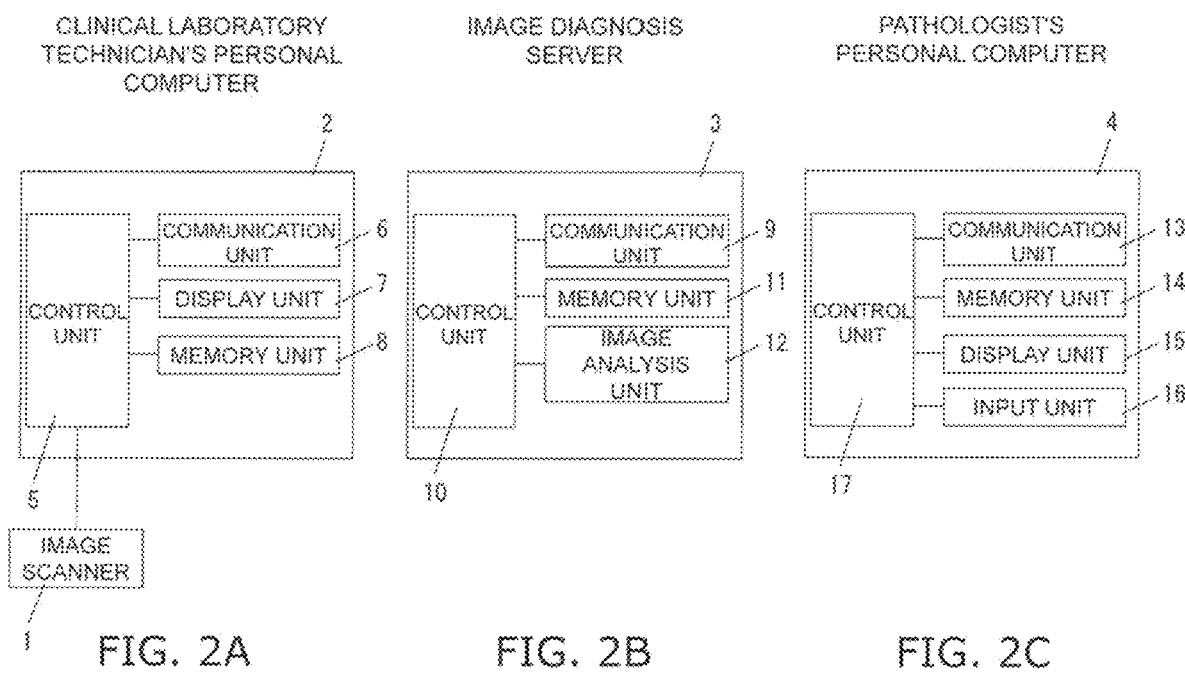
FIG. 2A is a control block diagram showing the configuration of a personal computer belonging to a clinical laboratory technician in FIG. 1.
FIG. 2B is a control block diagram showing the configuration of the image diagnosis server in FIG. 1.
FIG. 2C is a control block diagram showing the configuration of the personal computer of a pathologist in FIG. 1.

FIGS. 2A to 2C are control block diagram showing the configurations of the personal computer 2 belonging to a clinical laboratory technician, the image diagnosis server 3, and the pathologist's personal computer 4.

The personal computer 2 comprises a control unit 5 to which the image scanner 1 is connected, and a communication unit 6, a display unit 7, and a memory unit 8 that are connected to the control unit 5.

The image diagnosis server 3 includes a communication unit 9 that communicates with the communication unit 6 of the personal computer 2, a control unit (first control unit) 10 that is connected to the communication unit 9, a memory unit 11 that is connected to the control unit 10, and an image analysis unit 12 that analyzes a pathological diagnosis image. The control unit 10 controls the various units connected to the control unit 10. A control program for causing the control unit 10 to execute various operations is stored in a memory unit 11.

The pathologist's personal computer 4 comprises a communication unit 13 that communicates with the communication unit 9 of the image diagnosis server 3, a memory unit 14, a display unit 15, an input unit 16 to which display and other such control commands are inputted, and a control unit (second control unit) 17 to which all of these are connected. The control unit 17 controls the various units connected to the control unit 17. A control program for causing the control unit 17 to execute various operations is stored in the memory unit 14.

Figure 3:
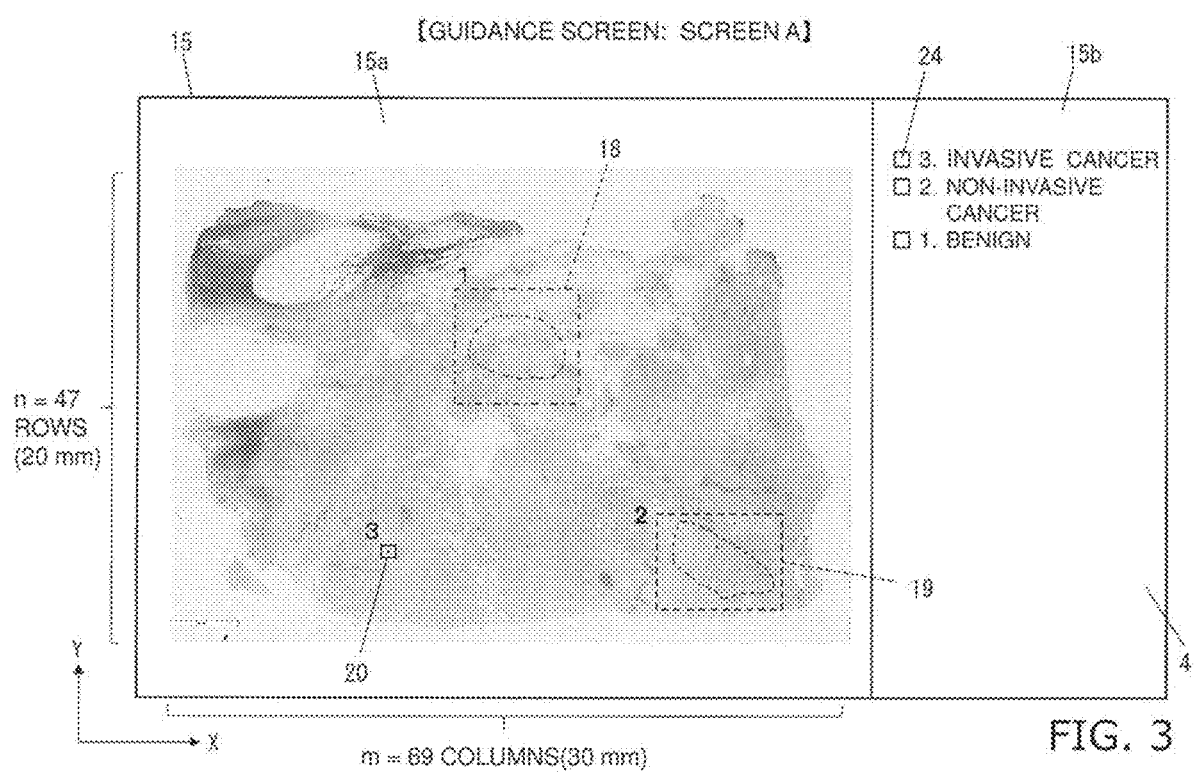
FIG. 3 is a diagram showing a display example of the display unit of the pathologist's personal computer in FIG. 1.

In this embodiment, an image such as that shown in FIG. 3 is displayed on the display unit 15 of the pathologist's personal computer 4. Then, the image diagnosis server 3 creates the following pathological diagnosis data in order to display this image on the display unit 15.

FIG. 3 shows the display screen of the display unit 15 displaying a viewer portion 15a that occupies most of the screen, and a guide portion 15b that is displayed on the right side of the viewer portion 15a.

The entire pathological diagnosis image is displayed on the viewer portion 15a.

Examples of what is displayed in the guide portion 15b as the abnormality reason and a frame number indicating that there is a point of interest to be checked in the pathological diagnosis image (discussed below) include "3. invasive cancer," "2. non-invasive cancer," and "1. benign."

The pathological diagnosis image displayed in the viewer portion 15a is sent to the image diagnosis server 3, and has a size of 30×20 mm, for example. This pathological diagnosis image is divided into m columns (69 columns) in the X direction and n rows (47 rows) in the Y direction by the image analysis unit 12, and the state after an abnormality determination has been made is displayed in the viewer portion 15a for each of these 3243 (=69×47) divided images.

Also, the image diagnosis server 3 calculates an abnormality score for each divided image, and forms a confirmation frame 18, a confirmation frame 19, and a confirmation frame 20 that include divided images whose abnormality score exceeds a threshold value. These confirmation frames 18, 19, and 20 are displayed together with frame numbers "1," "2," and "3" in the pathological diagnosis image.

Furthermore, the frame numbers "1," "2," and "3" of the confirmation frames 18, 19, and 20, and the abnormality reasons corresponding to these frame numbers are displayed in the guide portion 15b provided to the right of (outside) the pathological diagnosis image.

That is, in the confirmation frames (confirmation frames 18, 19, and 20 in FIG. 3) including divided images whose abnormal score exceeds the threshold value, the frame numbers "1," "2," and "3" and the corresponding reasons for the abnormality are displayed in the guide portion 15b, and the frame numbers "1," "2," and "3" and the confirmation frames 18, 19, and 20 are displayed in the viewer portion 15a.

Therefore, upon looking at the display unit 15 of the personal computer 4, the pathologist can immediately recognize from the frame numbers "1," "2," and "3" displayed in the guide portion 15b that there are three points of interest that should be checked in the pathological diagnosis image.

The position, size, and positional relationship of the confirmation frames 18 to 20 are formed can be immediately grasped from the three frame numbers "1," "2," and "3" and the three confirmation frames 18, 19, and 20 displayed in the pathological diagnosis image of the viewer portion 15a.

In all the confirmation frames 18, 19, and 20 displayed in the viewer portion 15a, only the frame line is displayed, and the inside of the frame is displayed in a visible state. This makes it easy to grasp the states of the three points of interest.

In the display example shown in FIG. 3, the frame numbers are represented by the numerals "1," "2," and "3," but the frame numbers may be anything so long as the confirmation frames 18, 19, and 20 can be specified. For example, letters, Roman numerals, icons, or a combination of these may be used as the frame numbers instead of numerals.

Also, in this embodiment, the guide portion 15b is provided outside and to the right of the pathological diagnosis image of the viewer portion 15a, but so-called window display may be performed outside the pathological diagnosis image, and the guide portion 15b may be provided in a window.

The processing performed by the personal computer 2 of the clinical laboratory technician, the image diagnosis server 3, and the personal computer 4 of the pathologist will now be described with reference to the flowcharts of FIGS. 9 and 10.

Figure 9:
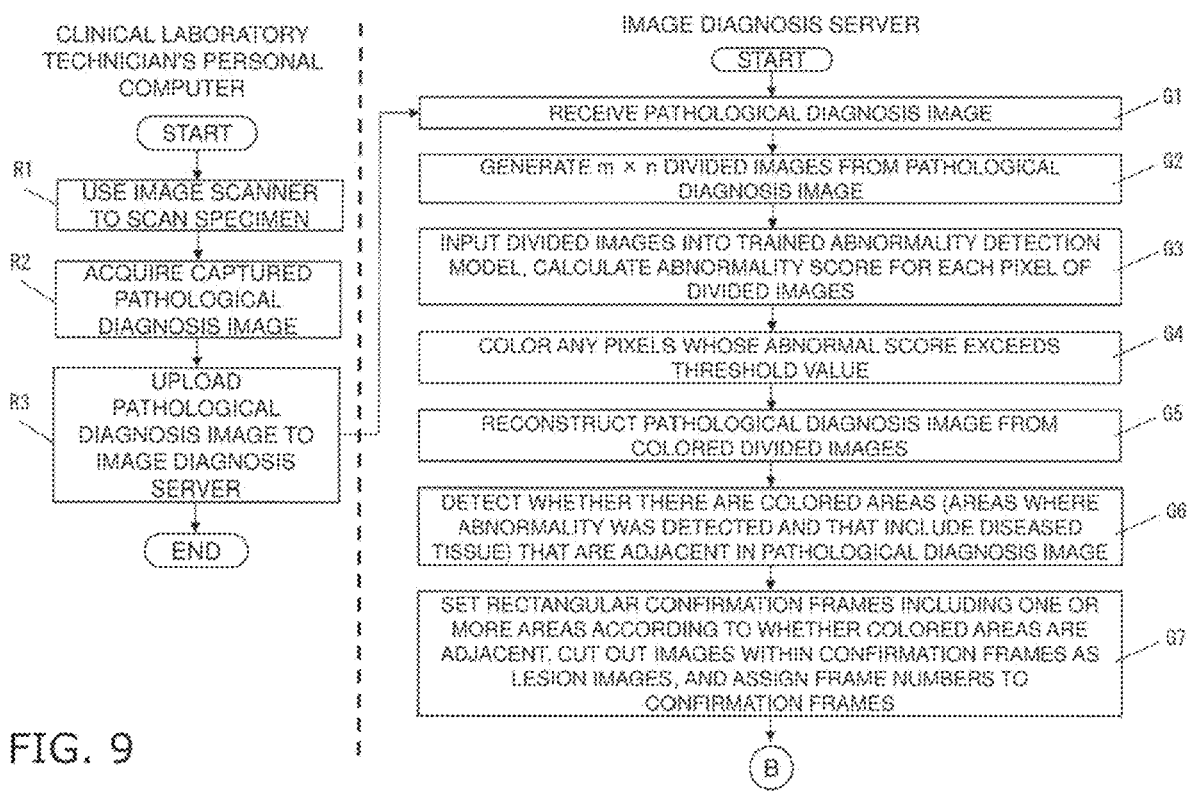
FIG. 9 is an operation flowchart of the personal computer of the clinical laboratory technician and the image diagnosis server in FIG. 1.

As shown in FIG. 9, the personal computer 2 is operated by a clinical laboratory technician to scan a pathological diagnosis specimen using the image scanner 1 (step R1), acquire this pathological diagnosis image (step R2), and then send the pathological diagnosis image to the image diagnosis server 3 (step R3).

When the control unit 10 of the image diagnosis server 3 receives the pathological diagnosis image (step G1), the image analysis unit 12 is used to generate m×n (3243 sections) divided images as discussed above (step G2).

Next, the control unit 10 inputs each divided image into a trained abnormality detection model, and calculates an abnormality score for each pixel of the divided images (step G3). The trained abnormality detection model is stored in advance in the memory unit 11 of the image diagnosis server 3.

Next, the control unit 10 colors any pixels whose abnormal score exceeds a threshold value (step G4).

Next, the control unit 10 collects 3243 sections of the colored divided images and reconstructs the pathological diagnosis image (step G5).

In the reconstructed pathological diagnosis image, a colored region indicates that an abnormality has been detected by the image analysis unit 12, and is a region with a high probability of containing diseased tissue. In other words, a colored region indicates that this is a point of interest that the pathologist will want to check more thoroughly.

The image analysis unit 12 detects whether or not there are colored divided images that are adjacent in the pathological diagnosis image (step G6). If some are adjacent, the rectangular confirmation frames 18, 19, and 20 are set in an integrated state, the images within the confirmation frames 18, 19, and 20 are cut out as lesion images, and each confirmation frame 18, 19, and 20 is assigned a frame number "1," "2," or "3" (step G7).

The higher up are the positions of the confirmation frames 18, 19, and 20 in the pathological diagnosis image, the lower is the frame number that is assigned.

Figure 10:
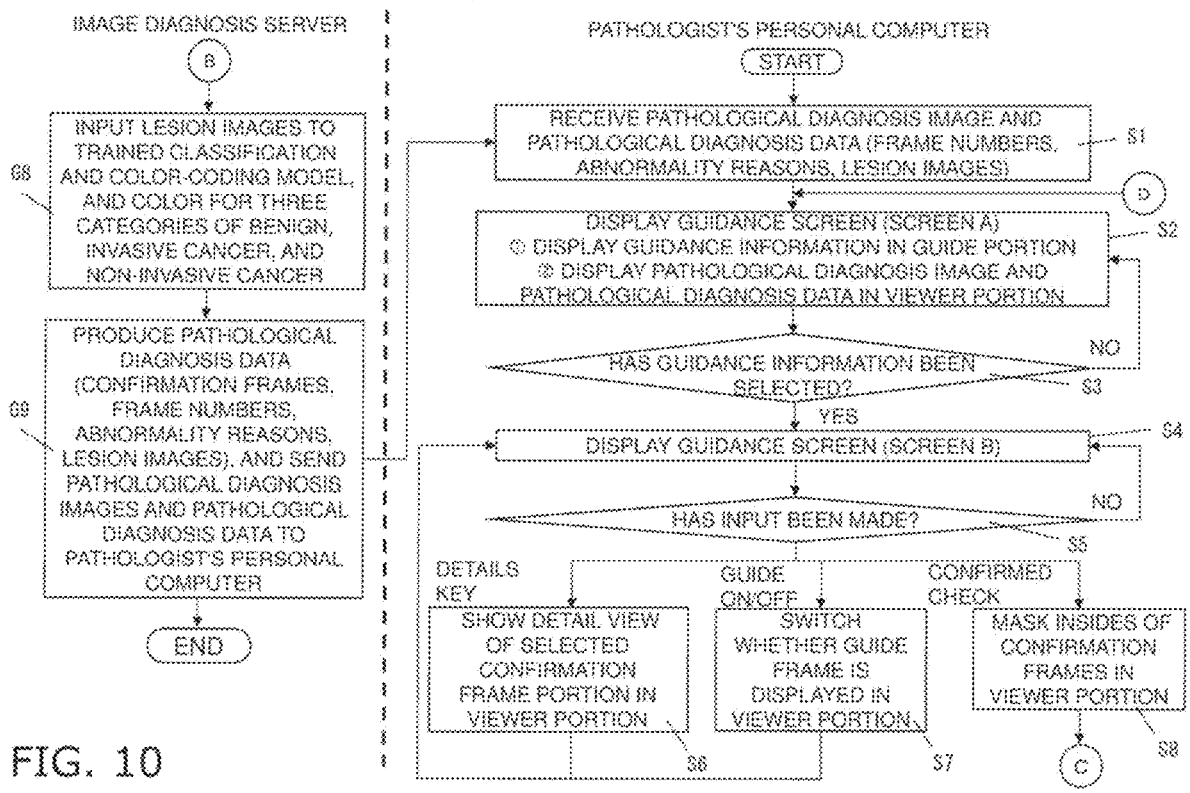
FIG. 10 is an operation flowchart of the image diagnosis server in FIG. 1 and the pathologist's personal computer.

Next, as shown in FIG. 10, the image diagnosis server 3 inputs a lesion image into a trained classification and color-coding model, determines the lesion area of the lesion image to have an abnormality reason of either "benign," "invasive cancer," or "non-invasive cancer," and decides on the color of the confirmation frame.

In this embodiment, for example, a confirmation frame for "benign" is red, a confirmation frame for "invasive cancer" is green, and a confirmation frame for "non-invasive cancer" is black. In this way, the reason for abnormality and the display color are assigned to each of the confirmation frames 18, 19, and 20 (step G8).

Next, the image diagnosis server 3 produces pathological diagnosis data including position information about the confirmation frames 18, 19, and 20 (example of setting information), frame numbers, abnormality reasons, display colors, and lesion images, and sends pathological diagnosis images and pathological diagnosis data to the pathologist's personal computer 4 (step G9).

The control unit 17 of the pathologist's personal computer 4 controls the display unit 15 so as to display the guidance screen A shown in FIG. 3 on the basis of the pathological diagnosis data received from the image diagnosis server 3 (steps S1 and S2).

On the guidance screen A shown in FIG. 3, the pathological diagnosis image is displayed in the viewer portion 15a, and the confirmation frames 18, 19, and 20 are displayed together with the frame numbers "1", "2," and "3" in the pathological diagnosis image. Also, the frame numbers "1", "2," and "3" of the confirmation frames 18, 19, and 20 are displayed together with the abnormality reasons "benign," "invasive cancer," and "non-invasive cancer" in the guide portion 15b provided to the right of and outside the pathological diagnosis image.

In FIG. 3, the confirmation frames 18 and 19 in the pathological diagnosis image are displayed as frames that are larger than the confirmation frame 20 because the images in the confirmation frames 18 and 19 are constituted by a plurality of divided images. On the other hand, the confirmation frame 20 displayed as a frame that is smaller than the confirmation frames 18 and 19 because it is constituted by just one divided image.

However, looking at the abnormality reason displayed in the guide portion 15b, we see that the abnormality reason for the frame number "3," which is the small confirmation frame 20, is "invasive cancer," and the risk is higher than that of the abnormality reason of "non-invasive cancer" for frame number "2," which is the large confirmation frame 19, and that of the abnormality reason of "benign" for frame number "1," which is a large confirmation frame 18.

That is, in this embodiment, regardless of the size of the confirmation frames 18 to 20, the frame numbers and the abnormality reasons are displayed in the guide portion 15b from highest to lowest, in descending order of risk. Consequently, in the guide portion 15b shown in FIG. 3, the frame number "3" of the confirmation frame 20 is displayed as the one with the highest risk.

The pathologist first selects frame number "3" in the guide portion 15b having the highest risk according to the content of the confirmation frames displayed in the guide portion 15b in descending order of risk. More specifically, frame number "3" is selected when the pathologist operates the input unit 16 to mark the line reading "3" invasive cancer" in the guide portion 15b. This results in the treatment screen B shown in FIG. 4 being displayed on the display unit 15 (steps S3 and S4 in FIG. 10).

Figure 4:
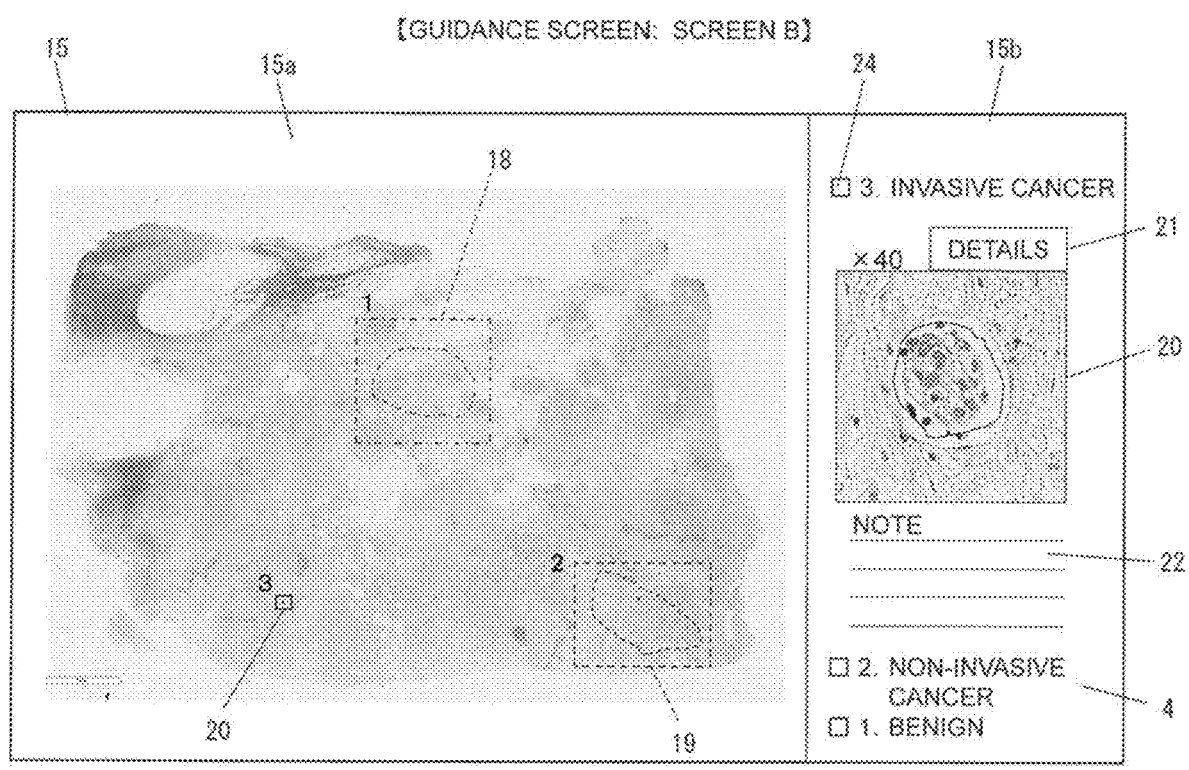
FIG. 4 is a diagram showing a display example of the display unit of the pathologist's personal computer in FIG. 1.

On the treatment screen B shown in FIG. 4, frame number "3" of the confirmation frame 20, the abnormality reason of "invasive cancer," and a 40-times magnified view of the confirmation frame 20 are displayed in the guide portion 15b.

The pathologist can check the treatment screen B and thereby recognize the risk of the confirmation frame 20 portion to which frame number "3" was assigned. Therefore, the pathologist clicks on a details key 21 in order to check the confirmation frame 20 more thoroughly.

Figure 5:
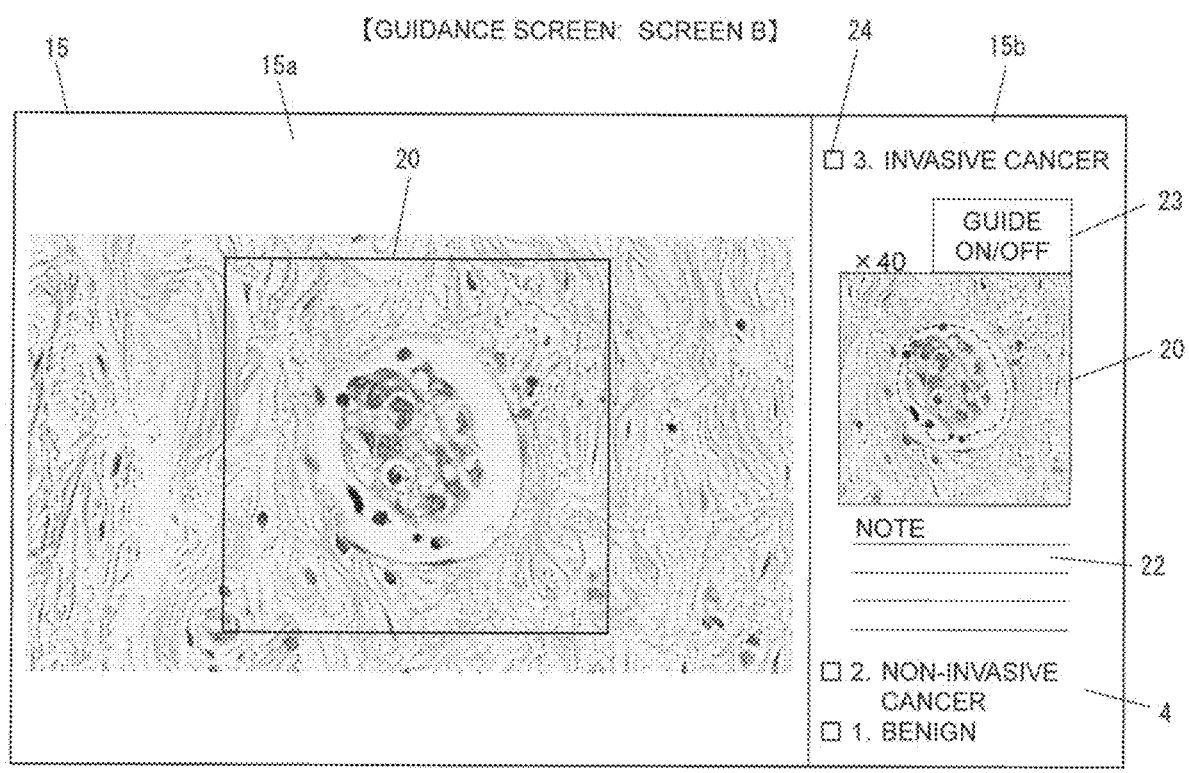
FIG. 5 is a diagram showing a display example of the display unit of the pathologist's personal computer in FIG. 1.

When the details key 21 is clicked, as shown in FIG. 5, a detail view of the confirmation frame 20 portion of the pathological diagnosis image is displayed in the viewer portion 15a of the display unit 15 (steps S5 and S6 in FIG. 10). Therefore, the pathologist thoroughly checks the pathological diagnosis image enlarged and displayed in the viewer portion 15a, and inputs a note in the note box 22.

If the pathologist wants to delete the confirmation frame 20 and continue checking, the pathologist operates the guide on/off key 23 to delete the confirmation frame 20 and continue checking (steps S5 and S7 in FIG. 10).

When the inputting of a note in the note box 22 is complete, the pathologist inputs a check mark in the input box 24 (an example of a confirmation input button) to indicate that frame number "3" has been checked (confirmed input).

The check input to the input box 24 means that the confirmation of the confirmation frame 20 corresponding to frame number "3" has been completed. When a check is inputted in the input box 24, information indicating that the confirmation frame 20 has been confirmed is assigned to that frame. Then, the confirmation frame 20 in which the confirmed input has been performed is subsequently displayed as being confirmed when displayed in the viewer portion 15a.

More specifically, the control unit 17 controls the display unit 15 so that the inside of the confirmation frame 20 is invisible (blacked out) and it can be seen that the confirmation has been completed (steps S5 and S8 in FIG. 10).

Figure 7:
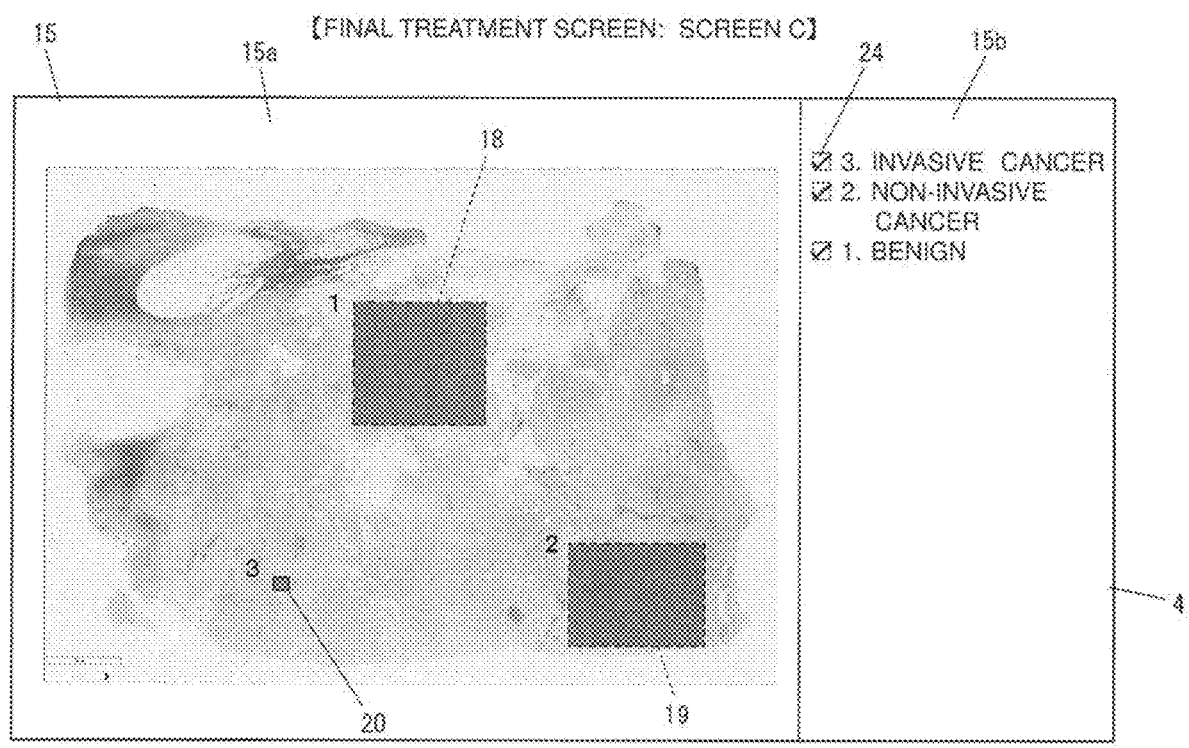
FIG. 7 is a diagram showing a display example of the display unit of the pathologist's personal computer in FIG. 1.

Then, the pathologist continues to confirm the confirmation frame 19 corresponding to frame number "2" having the second highest risk, and the confirmation frame 18 corresponding to frame number "1" having the third highest risk, and when this confirmation is finished, a final treatment screen C is displayed as shown in FIG. 7.

Figure 11:
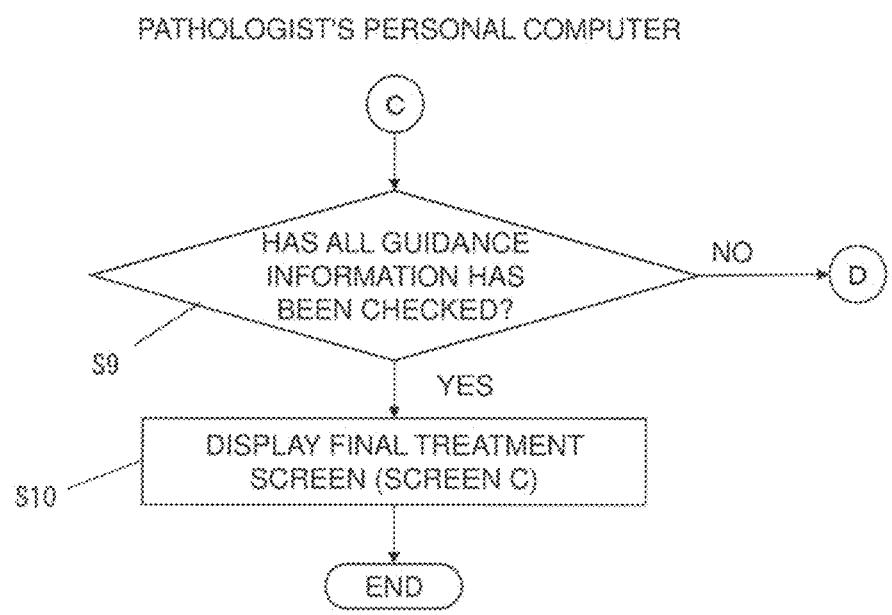
FIG. 11 is an operation flowchart of the pathologist's personal computer in FIG. 1.

More specifically, it is determined whether or not a check has been inputted in the input box 24 corresponding to the respective confirmation frames 18, 19, and 20, that is, whether or not all the guidance information has been checked (step S9 in FIG. 11). Once all the confirmations have been completed, the final treatment screen C is displayed (step S10 in FIG. 11).

In this embodiment, the control unit 17 controls the display unit 15 so that, in the pathological diagnosis image displayed in the viewer portion 15a, it can be seen that all the confirmation frames inputted as being confirmed have indeed been confirmed. Therefore, in FIG. 7, in the viewer portion 15a, the confirmation frame 20, the confirmation frame 19, and the confirmation frame 18 are displayed in an invisible state (blacked out) so that it can be seen that their confirmation has been completed.

On the other hand, if it is determined in step S9 of FIG. 11 that all the confirmations have not been completed, the processing goes back to step S2 in FIG. 10, and the processing from step S2 onward is repeated.

The invisible state here is represented by a frame that has been blacked out, but the invisible state may be any state in which the inside of the frame cannot be accurately recognized. For instance, the inside of the frame may be made semi-transparent, or diagonal lines may be displayed in the frame, so that the inside of the frame cannot be recognized accurately.

As discussed above, with the pathological diagnosis support system of this embodiment, when the pathologist starts the diagnosis of the pathological diagnosis image, the frame numbers "1," "2," and "3" and the corresponding abnormality reasons are displayed in the guide portion 15b has as shown in FIG. 3. Therefore, the pathologist can easily recognize that there are three points of interest to be confirmed in the pathological diagnosis image.

Then, the position, size, and positional relationship of the confirmation frames 18, 19, and 20 in the pathological diagnosis image can be grasped immediately from the confirmation frames 18, 19, and 20 and frame numbers "1," "2," and "3" displayed in the pathological diagnosis image. At this point, only the frame lines of the confirmation frames 18, 19 and 20 are displayed, and the inside of the frames is displayed in a visible state, so it is also easy to grasp the state of the points of interest.

Therefore, the pathologist can intentionally do a thorough check of the confirmation frames 18, 19, and 20.

In other words, since the confirmation frames 18, 19, and 20 and the frame numbers "1," "2," and "3" are displayed at the points of interest to be checked, there is less risk that the pathologist will overlook these parts, and the pathologist can also feel more confident and assured about the confirmation, so the burden on the pathologist can be reduced.

Once diagnosis of the point of interest is complete, the pathologist checks the parts other than the confirmation frames 18, 19, and 20 by using the viewer portion 15a so that nothing is omitted in the pathological diagnosis.

In this embodiment, as shown in FIG. 7, when the plurality of confirmation frames 18, 19, and 20 are displayed in the pathological diagnosis image displayed in the viewer portion 15a, all of the confirmation frames 18, 19, and 20 for which confirmed input have been performed are displayed in a state in which the contents of the frames are invisible.

Consequently, the pathologist can recognize at a glance any remaining parts to be checked (sites other than the confirmation frames 18, 19, and 20), and this further reduces the burden on the pathologist.

Figure 8:
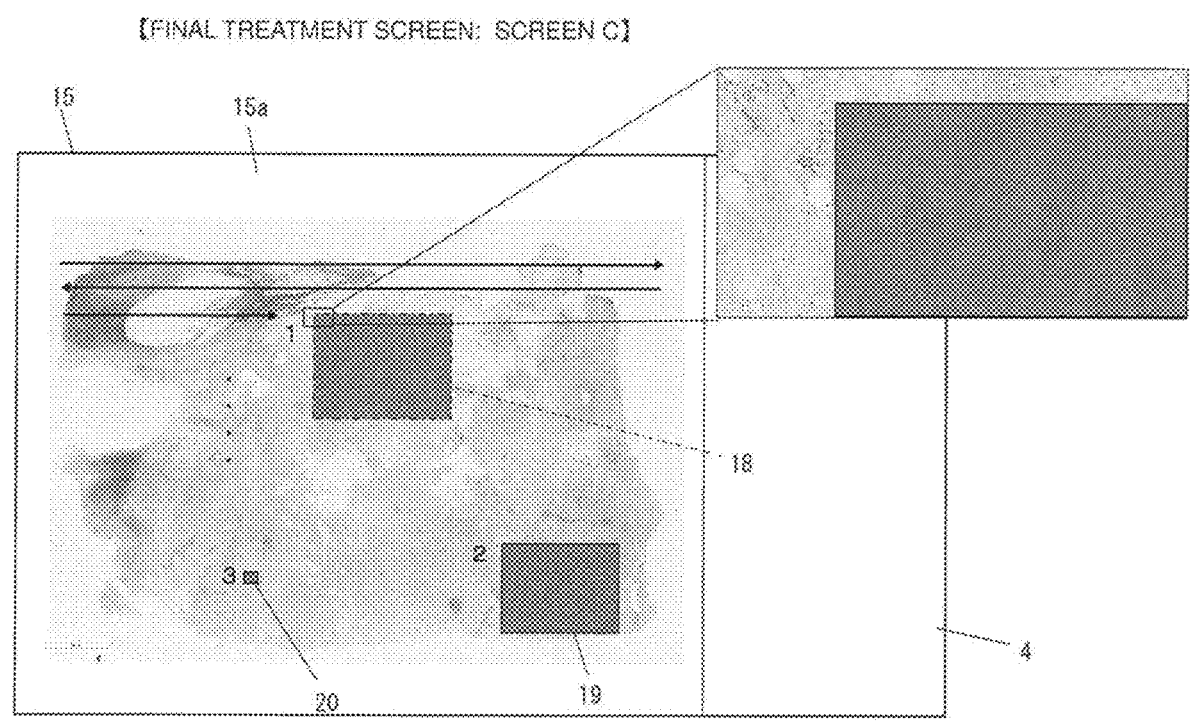
FIG. 8 is a diagram showing a display example of the display unit of the pathologist's personal computer in FIG. 1.

More specifically, as shown in FIG. 8, just as in the past, if there are any suspicious points other than those displayed in the guide portion 15b while the pathologist moves his line of sight in the horizontal direction along each row from the upper side to the lower side, those areas are enlarged and checked at the corresponding positions.

In this embodiment, as shown in the upper-right part of FIG. 8, when the pathological diagnosis image is enlarged and displayed on the display unit 15, all the confirmation frames for which the confirmed input has been performed are displayed as being confirmed. Here, of the confirmation frames 18, 19, and 20 for which confirmed input has been performed, the confirmation frame 18 enlarged and displayed on the display unit 15 is displayed in an invisible state, which indicates that the confirmation has already been done.

As described above, even when the enlarged confirmation work is carried out at a position corresponding to a suspicious point, the fact that the confirmation frame 18, for which the confirmation work is most needed, has already been confirmed is displayed in an invisible state. Accordingly, the pathologist can be assured that "the confirmation of this part is definitely completed." Then, any other parts can be confirmed one after the other, smoothly and calmly, and the burden on the pathologist can be further reduced.

Figure 6:
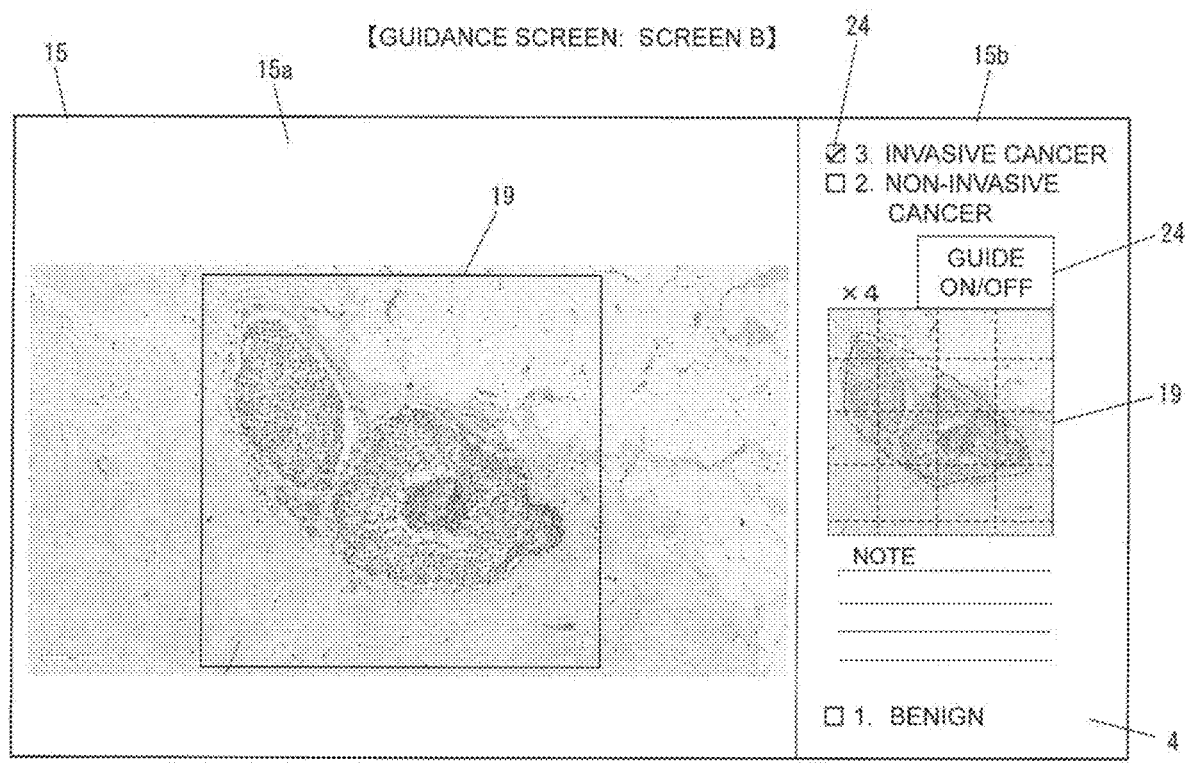
FIG. 6 is a diagram showing a display example of the display unit of the pathologist's personal computer in FIG. 1.

FIG. 6 shows the treatment screen B of the portion of the confirmation frame 19 with the frame number "2."

There are a plurality of divided images in the confirmation frame 19 of the guide portion 15*b*, indicating that the region where an abnormality was detected is large. At this point, the confirmation frame 19 of the viewer portion 15*a* is displayed in a state in which there are a plurality of divided images in the confirmation frame 19.

Accordingly, even when an abnormality is detected in a large area, since the confirmation frame 19 set to an appropriate range (size) will be displayed in the viewer portion 15*a*, the pathologist can easily recognize the position and range of the point of interest.

The pathologist checks the confirmation frame 19 while using a zoom key (not shown) to display the pathological diagnosis image in the viewer portion 15*a* in an enlarged or reduced form, for example.

Figure 12:
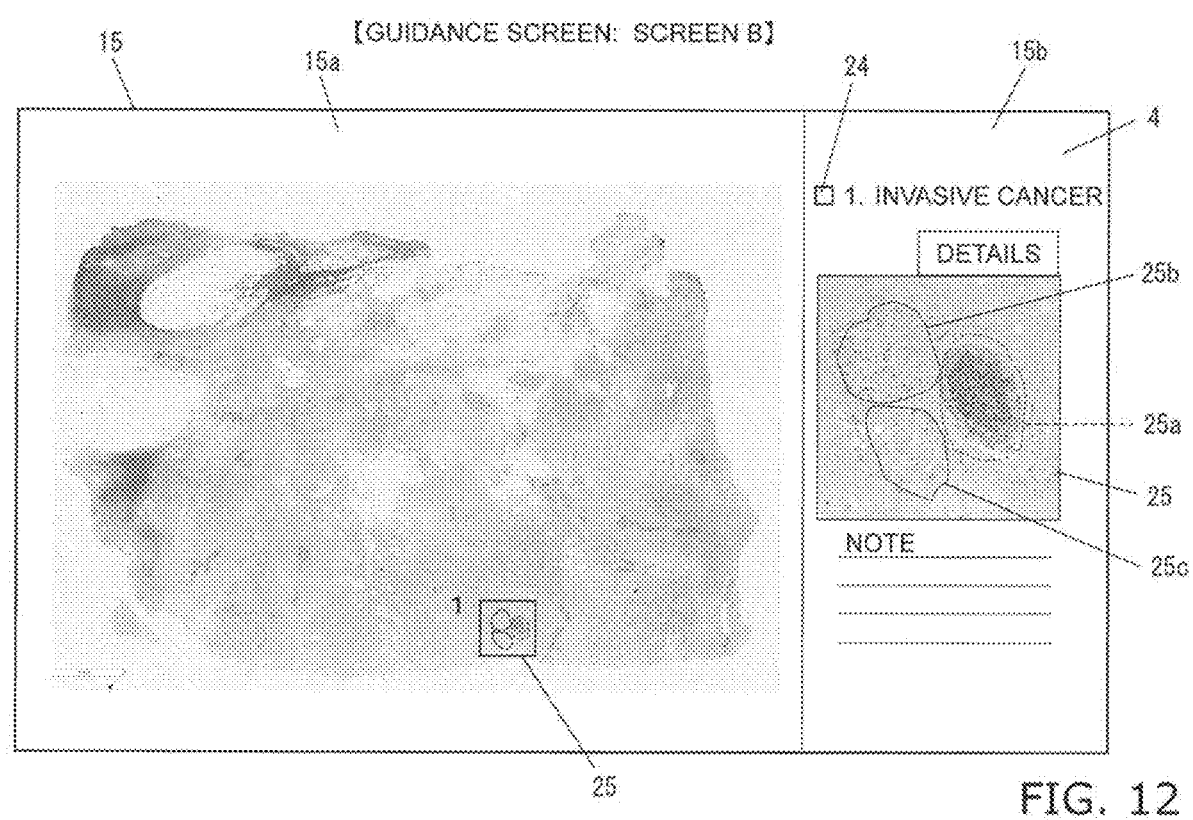
FIG. 12 is a diagram showing a display example of the display unit of the pathologist's personal computer in FIG. 1.

FIG. 12 shows the treatment screen B of a confirmation frame 25.

A plurality of lesion areas, namely, a "benign" lesion area 25*a*, an "invasive cancer" lesion area 25*b*, and an "invasive cancer" lesion area 25*c* are displayed in the confirmation frame 25.

Thus, when a plurality of lesion areas are included in a single confirmation frame 25, the image analysis unit 12 sets the abnormality reason for the confirmation frame 25 to the abnormality reason having the highest risk. That is, the image analysis unit 12 sets the abnormality reason for the confirmation frame 25 to "invasive cancer."

Then, when the confirmation frame 25 including a plurality of divided images is displayed on the display unit 15 of the pathologist's personal computer 4, as shown in FIG. 12, the abnormality reason with the highest risk out of the abnormality reasons with respect to the divided images in the confirmation frame 25 is displayed in a region outside the pathological diagnosis image (that is, the guide portion 15*b*).

Therefore, the display takes safety into account so that the pathologist will not easily overlook it, and this again reduces the burden on the pathologist.

Figure 13:
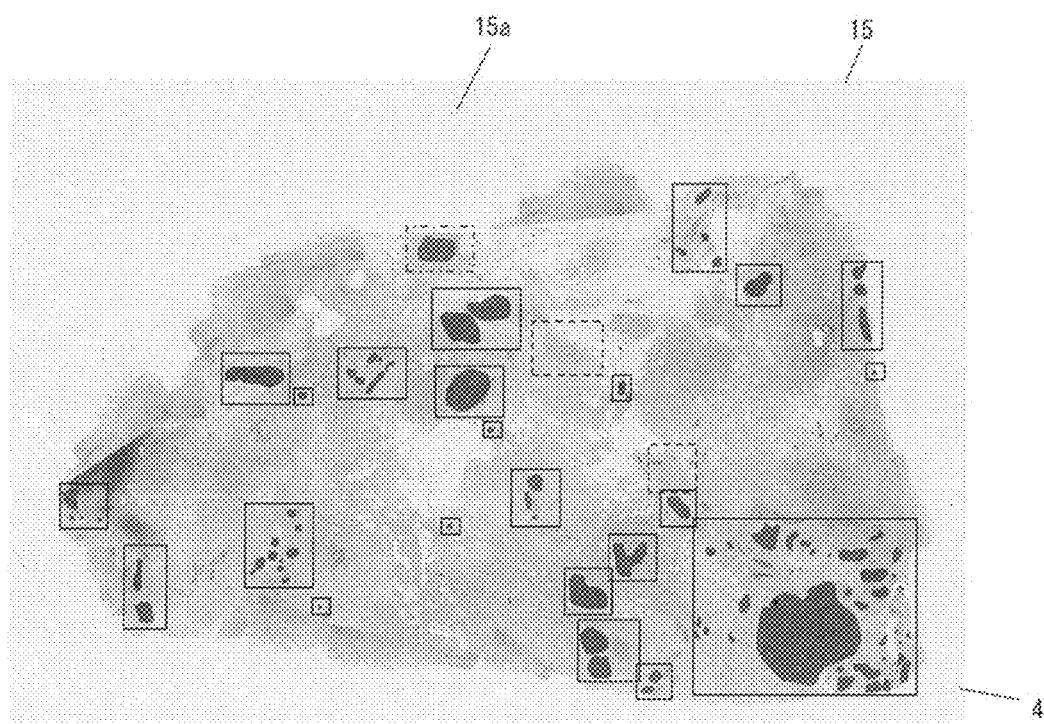
FIG. 13 is a diagram showing a display example of the display unit of the pathologist's personal computer in FIG. 1.
Figure 14:
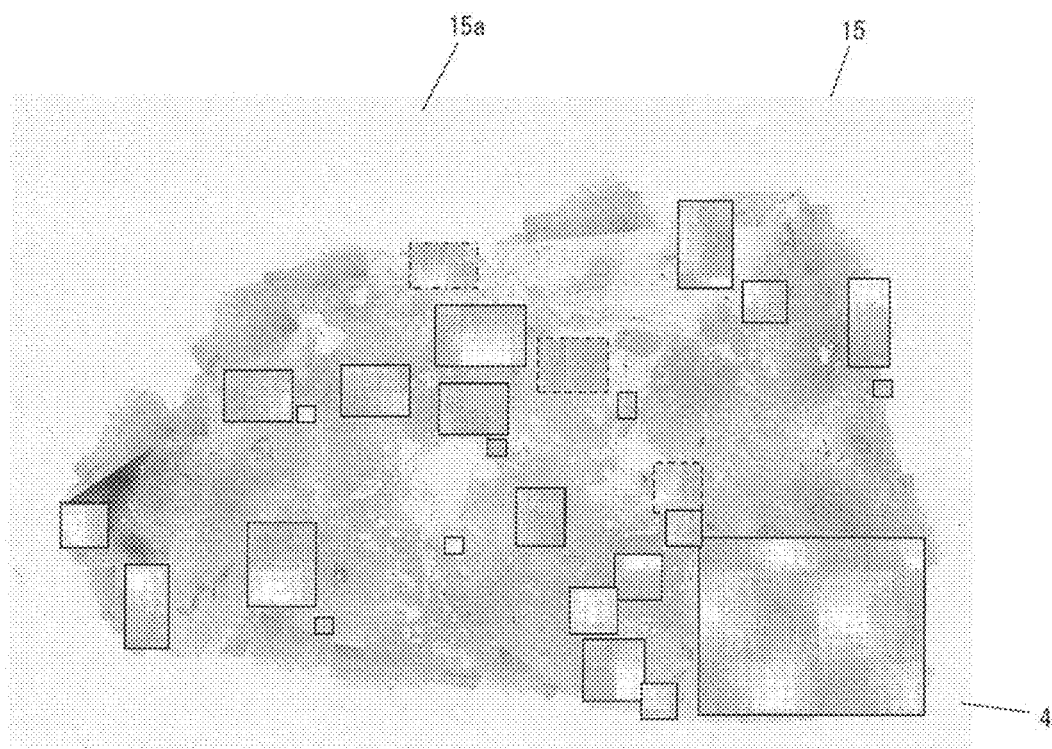
FIG. 14 is a diagram showing a display example of the display unit of the pathologist's personal computer in FIG. 1.

FIGS. 13 and 14 show a state in which many confirmation frames are present in the pathological diagnosis image. Even when there are so many confirmation frames, the risk that the pathologist will overlook any of them can be reduced by assigning frame numbers and abnormality reasons to each confirmation frame, and providing confirmation guidance to the guide portion 15*b*.

In other words, not only are the parts to be confirmed by the pathologist simply colored, but also frame numbers for confirmation and abnormality reasons are assigned and guidance is displayed, and this prevents any parts that are supposed to be confirmed by the pathologist from being overlooked.

Also, as shown in FIG. 14, since display control is performed so that confirmed confirmation frames are displayed in an invisible state (blacked out), it is easy to ascertain whether or not all the confirmation frames have been confirmed, so anxiety about whether or not any confirmations have been skipped can be eliminated.

Since there are many confirmation frames in FIGS. 13 and 14, the frame numbers for the confirmation frame are not shown in an effort to maintain the legibility of the drawings, but in actual practice confirmation frame and frame numbers are displayed in the pathological diagnosis image, and the frame numbers and abnormality reasons are displayed in the guide portion 15*b*.

Embodiment 2

The pathological diagnosis support device according to another embodiment of the present invention will now be described with reference to FIGS. 15 to 17.

Figure 15:
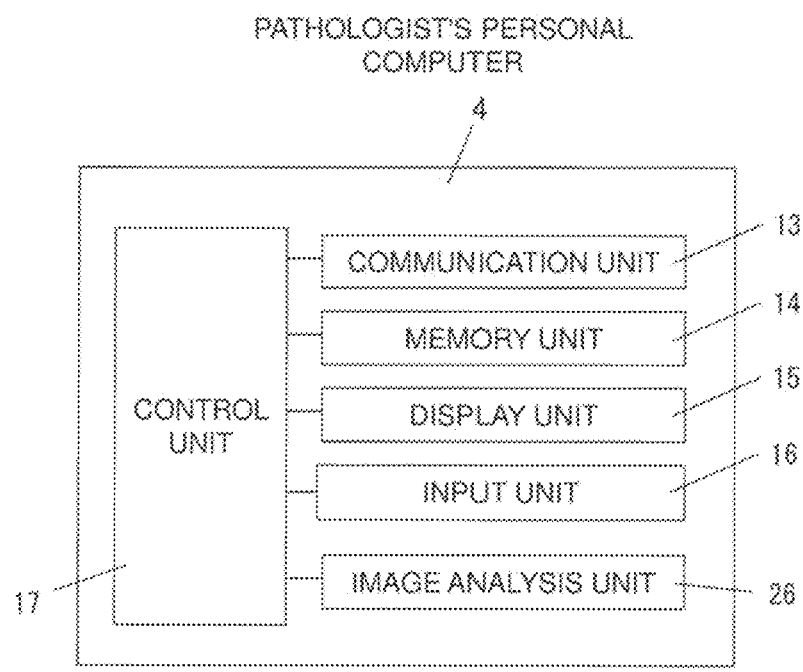
FIG. 15 is a control block diagram showing the configuration of the pathologist's personal computer according to Embodiment 2 of the present invention.

Specifically, in Embodiment 1 above, the configuration was such that the image analysis unit 12 of the image diagnosis server 3 analyzed the pathological diagnosis image, but as shown in FIG. 15, the configuration may instead be such that an image analysis unit 26 is provided to the personal computer 4 of Embodiment 1 (an example of a pathological diagnosis support device), and the analysis of pathological diagnosis images is performed on the pathologist's personal computer 4.

That is, as shown in FIG. 15, the pathologist's personal computer 4 comprises an image analysis unit 26 that analyzes pathological diagnosis images, a control unit (third control unit) 17 to which the image analysis unit 26 is connected, and the communication unit 13, the memory unit 14, and the display unit 15 that are connected to the control unit 17.

The control unit 17 uses the image analysis unit 26 to divide the pathological diagnosis image into a plurality of divided images, calculate an abnormality score for each divided image, set confirmation frames including divided images whose abnormality score exceeds a threshold value, and assign a frame number to each of the confirmation frames. Then, when the pathological diagnosis image is displayed on the display unit 15, the control unit 17 displays the confirmation frame and the corresponding frame number on the pathological diagnosis image, and displays the frame number of the confirmation frame outside of the pathological diagnosis image.

In this embodiment, when a pathological diagnosis image is sent from the image diagnosis server 3 to the pathologist's personal computer 4, the image analysis unit 26 performs the same analysis operation as the image analysis unit 12 of the image diagnosis server 3 in Embodiment 1 above. That is, the image analysis unit 26 performs the analysis operation of steps G1 to G7 in FIG. 9 and steps G8 and G9 in FIG. 10.

After this, the personal computer 4 performs the same operation as in Embodiment 1.

Consequently, the effect obtained in Embodiment 1 can also be obtained in this embodiment.

Here, the pathological diagnosis support system of Embodiment 1 and the pathological diagnosis support device of Embodiment 2 are also applied to pathological diagnosis (including histological diagnosis and cytodiagnosis) of breast cancer and the like, for example.

Figure 16:
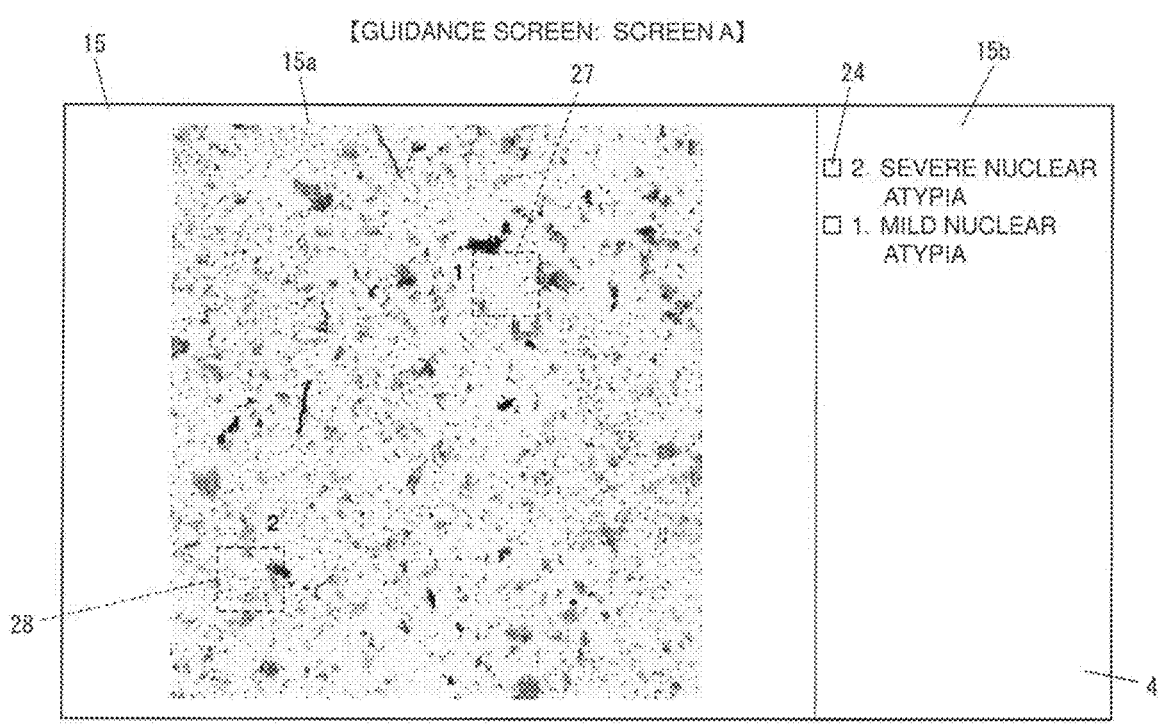
FIG. 16 is a diagram showing a display example of the display unit of the pathologist's personal computer in FIG. 1.
Figure 17:
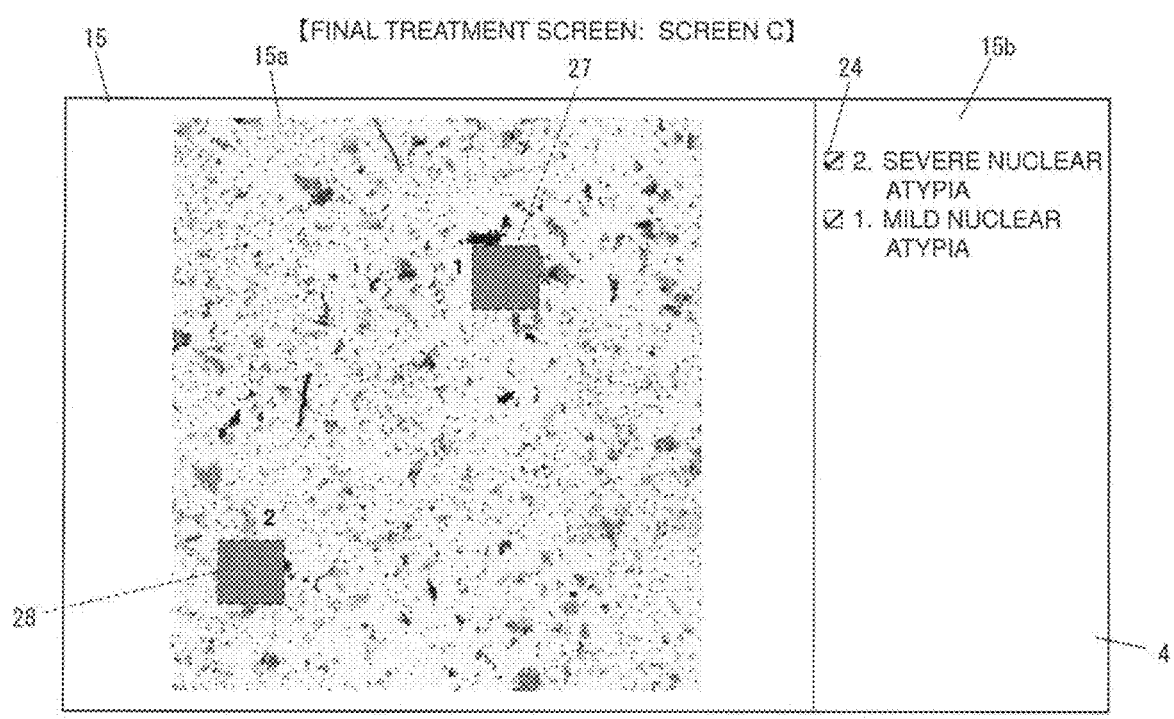
FIG. 17 is a diagram showing a display example of the display unit of the pathologist's personal computer in FIG. 1.

More specifically, FIGS. 16 and 17 are images displayed on the personal computer 4 when a cytodiagnosis of breast cancer is performed, and a cell image is displayed in the viewer portion 15*a* as a pathological diagnosis image. This cell image is acquired by extended depth of focus, and is an image obtained by capturing a plurality of images by slightly shifting the focal position each time a pathological diagnosis specimen is imaged, and combining just those places where these multiple images were in focus.

When such a cytodiagnosis is performed, as shown in FIG. 16, when the pathologist starts the diagnosis of the pathological diagnosis image, frame numbers and abnormality reasons are displayed in the guide portion 15b in descending order of risk.

More specifically, the reasons for abnormalities, such as "2. Severe nuclear atypia" and "1. Mild nuclear atypia," and the respective input boxes 24 (an example of a confirmation input button) are displayed.

In the viewer portion 15a are displayed the confirmation frame 27 corresponding to frame number "1" along with frame number "1," and the confirmation frame 28 corresponding to frame number "2" along with frame number "2."

Therefore, the pathologist can easily recognize the positions of the confirmation frames 27 and 28 (which are the points of interest), the range over which abnormal cells are present, and the positional relationship.

Also, in this case, since only the frame lines of the confirmation frames 27 and 28 are displayed, and the insides of the frame are displayed in a visible state, the state in the frame can be easily ascertained. That is, in the case of a cytodiagnosis, the findings that the pathologist should examine are the state of the cell nuclei, the layout and color of the cells, and so forth. Therefore, it can be easily recognized that notable features (state of cell nuclei, and the layout and color of cells) are in the confirmation frames 27 and 28.

As a result, the pathologist can perform a thorough pathological diagnosis on the confirmation frames 27 and 28 after having ascertained the state of the confirmation frames 27 and 28.

After this, when diagnosis of the points of interest is complete, the pathologist uses the viewer portion 15a to check portions other than the confirmation frames 27 and 28, so that the pathological diagnosis will not miss anything.

At this point, as shown in FIG. 17, in the pathological diagnosis image in the viewer portion 15a, the contents of the confirmation frames 27 and 28 for which confirmed input has been made are all displayed in an invisible state.

Consequently, the pathologist can recognize at a glance what remains to be checked (sites other than the confirmation frames 27 and 28), and this reduces the burden on the pathologist.

INDUSTRIAL APPLICABILITY

The present invention is anticipated to find use as a pathological diagnosis support system and a pathological diagnosis support device used for pathological diagnosis of cancer, for example.

REFERENCE SIGNS LIST 1 image scanner
2 personal computer
3 image diagnosis server
4 personal computer (an example of a pathologist's terminal)
5 control unit
6 communication unit
7 display unit
8 memory unit
9 communication unit
10 control unit (first control unit)
11 memory unit
12 image analysis unit
13 communication unit
14 memory unit
15 display unit
15a viewer portion
15b guide portion
16 input unit
17 control unit (second control unit, third control unit)
18 confirmation frame
19 confirmation frame
20 confirmation frame
21 details key
22 note box
23 guide on/off key
24 input box (example of confirmed input button)
25 confirmation frame
25a lesion area
25b lesion area
25c lesion area
26 image analysis unit
27 confirmation frame
28 confirmation frame

The invention claimed is:

1. A pathological diagnosis image display device that displays a pathological diagnosis image and a confirmation frame including the pathological diagnosis image whose abnormality score exceeds a threshold value, the pathological diagnosis image display device comprising:

a display unit; and a control unit configured to control the display unit so that when the pathological diagnosis image is displayed on the display unit, a confirmation input button, with which a confirmed input indicating a completion of confirmation of the confirmation frame, is displayed outside of the pathological diagnosis image and the confirmation frame is displayed inside of the pathological diagnosis image and an inside of the confirmation frame is displayed in a visible state, wherein the control unit displays the confirmation input button and causes a user to perform the confirmed input, and controls the display unit to display the confirmation frame in which the confirmed input has been made when the confirmation frame is displayed on the display unit, and the control unit controls the display unit so that an inside of the confirmation frame for which confirmed input has been performed is displayed such that the pathological diagnosis image in the confirmation frame in an invisible state, and the control unit controls the display unit so that the pathological diagnosis image in an area of the confirmation frame where the confirmed input has been made is displayed in an invisible state when an enlarged image of the pathological diagnosis image is displayed in the display unit.

2. The pathological diagnosis image display device according to claim 1, wherein the control unit controls the display unit so that when a plurality of the confirmation frames are displayed on the display unit, it can be seen that all the confirmation frames for which the confirmed input has been performed have been confirmed.

* * * * *